US00PP26190P3

(12) United States Plant Patent
Egger

(10) Patent No.: US PP26,190 P3
(45) Date of Patent: Dec. 1, 2015

(54) ***SEDUM* PLANT NAMED 'ROSETTA'**

(50) Latin Name: *Sedum telephium* (Syn. *Hylotelephium telephium*)
Varietal Denomination: Rosetta

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 120 days.

(21) Appl. No.: 13/987,669

(22) Filed: Aug. 20, 2013

(65) Prior Publication Data

US 2015/0059040 P1 Feb. 26, 2015

(51) Int. Cl.
*A01H 5/02* (2006.01)

(52) U.S. Cl.
USPC ..... Plt./479

(58) Field of Classification Search
USPC ..... Plt./479
See application file for complete search history.

(56) References Cited

PUBLICATIONS

Greenhouse Grower, Apr. 22, 2013.*

* cited by examiner

*Primary Examiner* — Keith O. Robinson
(74) *Attorney, Agent, or Firm* — Klarquist Sparkman, LLP

(57) ABSTRACT

A new and distinct hybrid of *Sedum* plant substantially as shown and described, with blue green leaves, spring growth with opening leaves that look like cabbages, cream colored flowers in medium inflorescences, a medium, upright, arching habit, and excellent vigor.

2 Drawing Sheets

Botanical denomination: *Sedum telephium* (Syn. *Hylotelephium telephium*).
Variety designation: 'Rosetta'.

BACKGROUND OF THE INVENTION

The present invention relates to a new and distinct cultivar of *Sedum telephium* and given the cultivar name of 'Rosetta'. *Sedum* is in the family Crassulaceae. The new cultivar is part of a planned breeding program to make short, compact, multicrown plants. The new cultivar originated from a controlled cross of a proprietary seedlings, 29-5, as the seed parent, and 29-6, as the pollen parent.

Compared to the seed parent, *Sedum* 29-5, the new cultivar is shorter and has much better quality foliage. Compared to the pollen parent, *Sedum* 29-6, the new cultivar has a smaller, bluer green leaves, and a better habit.

Compared to *Sedum* 'Hab Gray', an unpatented plant, the new variety has smaller leaves, shorter internodes, and is more upright.

This new and unique *Sedum* is distinguished by:

1. blue green leaves,
2. spring growth with opening leaves that look like cabbages,
3. cream colored flowers in medium inflorescences,
4. a medium, upright, arching habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the foliage of a 3 year old *Sedum* 'Rosetta' growing in the trial field in mid May in Canby, Oreg.

FIG. 2 shows the same plant in late June.

FIG. 3 shows a 9 month old *Sedum* 'Rosetta' in bloom in the trial field in late September in Canby, Oreg.

FIG. 4 shows the mature habit on a 4 year old *Sedum* Rosetta' in the trial field in seed in mid October in Canby, Oreg.

DETAILED PLANT DESCRIPTION

The following is a detailed description of the new *Sedum* hybrid based on observations of a four year old specimen grown in the trial field in full sun under typical outdoor conditions in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* 5$^{th}$ edition, 2007.

Plant:

*Type.*—Herbaceous perennial.
*Hardiness.*—USDA Zone 4 to 9.
*Size.*—55 cm tall from the ground to the base of the inflorescence and 91 cm wide.
*Habit.*—Upright.
*Vigor.*—Excellent.

*Roots and rooting.*—Main roots thick, with secondary roots dense and fibrous, color closest to Brown N200C in color; plants initiate roots in 10 days and produce a rooted plant in 4 weeks.

Stem:

*Number.*—54.
*Size.*—45 cm long and 19 mm wide.
*Internode length.*—1 cm long.
*Color.*—Yellow Green 147D.
*Texture.*—Succulent.
*Surface.*—Glabrous.

Leaf:

*Type.*—Simple.
*Arrangement.*—Variable.
*Shape.*—Ovate.
*Apex.*—Obtuse.
*Base.*—Obtuse.
*Venation.*—Pinnate.
*Margins.*—Irregularly serrate to entire.
*Blade size.*—Grows to 6.5 cm long and 4.7 cm wide.
*Surface.*—Glabrous and matte on both sides.
*Texture whole leaf.*—Thick, spongy, succulent.
*Petiole.*—Leaves sessile.
*Leaf color.*—Topside between Greyed Green 189A and Yellow Green 147B with the vein Yellow Green 147D; bottom side closest to Greyed Green 191A with vein Yellow Green 147D.

Inflorescence:

*Type.*—Terminal, corymbose, umbel-like.
*Number of flowers.*—500 to 1000 per stem (increases with age).
*Pedicels.*—1 mm to 2.5 mm long, 1 mm wide, glabrous, Yellow Green 148C.
*Peduncle.*—Grows to 7 cm tall and 8 mm wide, Yellow Green 147C tinted Greyed Purple 187B in sun, glabrous.
*Size.*—Grows to 21 cm deep and 15 cm wide.
*Bloom period.*—August through September in Canby, Oreg.

Flower bud:

*Size.*—3 mm wide, 3 mm deep.
*Description.*—Ovoid.
*Color.*—White 155C tinted Greyed Purple 183C at top.

Flower:

*Type.*—Actinomorphic.
*Shape.*—Stellate.
*Size.*—5 mm deep and 6 mm wide.
*Corolla description.*—5 mm deep and 6 mm wide, 5 petals, each elliptical, 5 mm long and 2 mm wide, margins entire, tip acuminate, glabrous on both sides, top and bottom side White NN155C with the main vein on back side tinted Greyed Purple 183C at top.
*Calyx description.*—1 mm deep and 2.5 mm wide, stellate, 5 lobes, divided to the base, margins entire, tip acute, glabrous, Yellow Green 148C on both sides.
*Stamen description.*—10 in number, 4.2 mm long, filaments 3 mm long and White 155C, anthers sterile and reduced, no pollen.
*Pistil description.*—5 separate prominent carpels, each 3 mm deep and 1.5 mm wide, Yellow Green 145C overall, style less than 1 mm long.
*Fragrance.*—None.
*Lastingness.*—Each stem lasts up to a month.

Fruit:

*Type.*—Ventrally dehiscent follicle, erect, attenuate.
*Fertility.*—Low.
*Size.*—3 mm wide and 3 mm deep.
*Color.*—Greyed Orange 165A.

Seed: None seen.

Disease and pest resistance or tolerance: Pest and disease resistance are typical for this type of *Sedum*.

I claim:

1. A new and distinct hybrid of *Sedum* plant as herein illustrated and described.

* * * * *

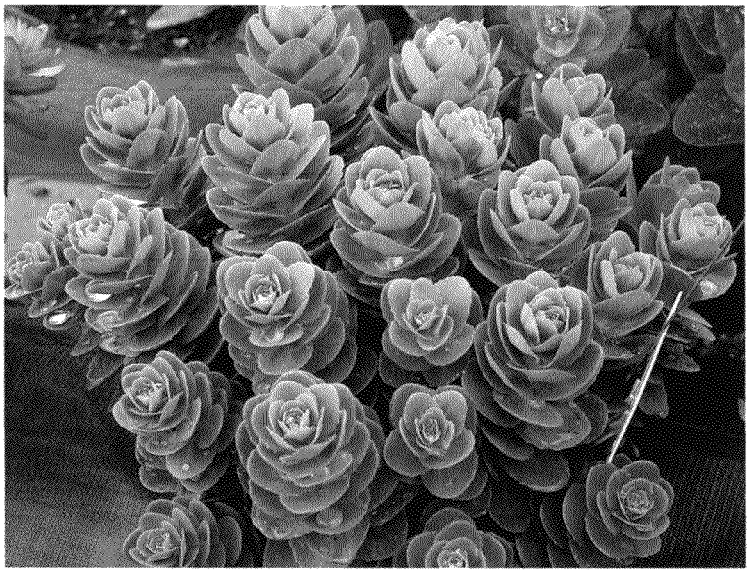
FIG.1 on left
FIG. 2 below
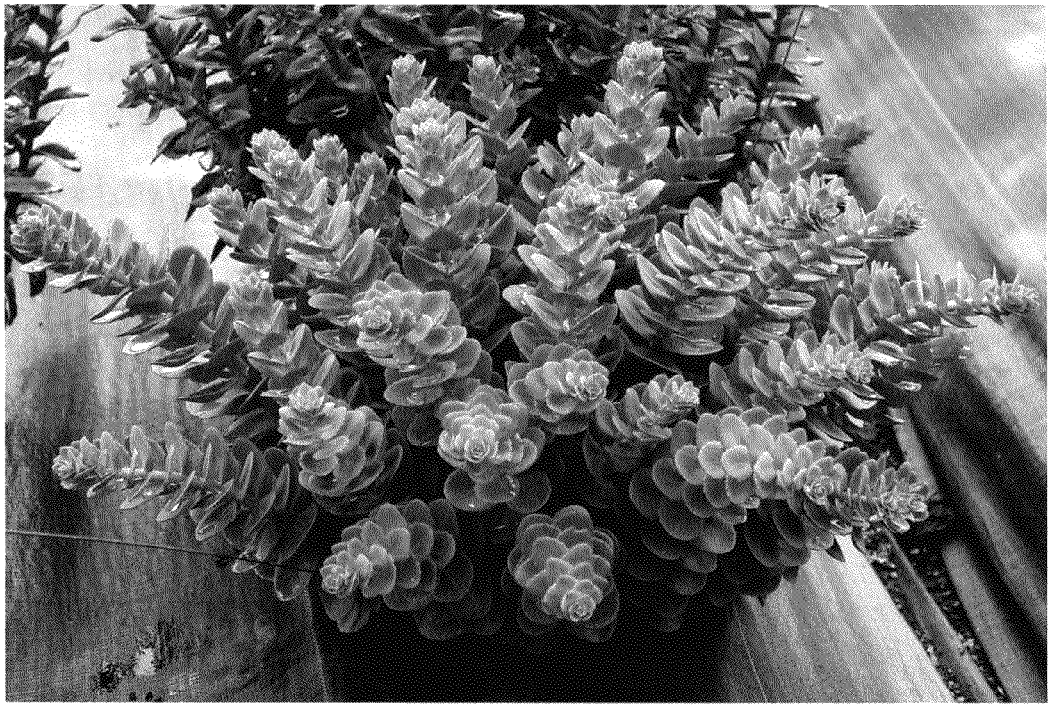

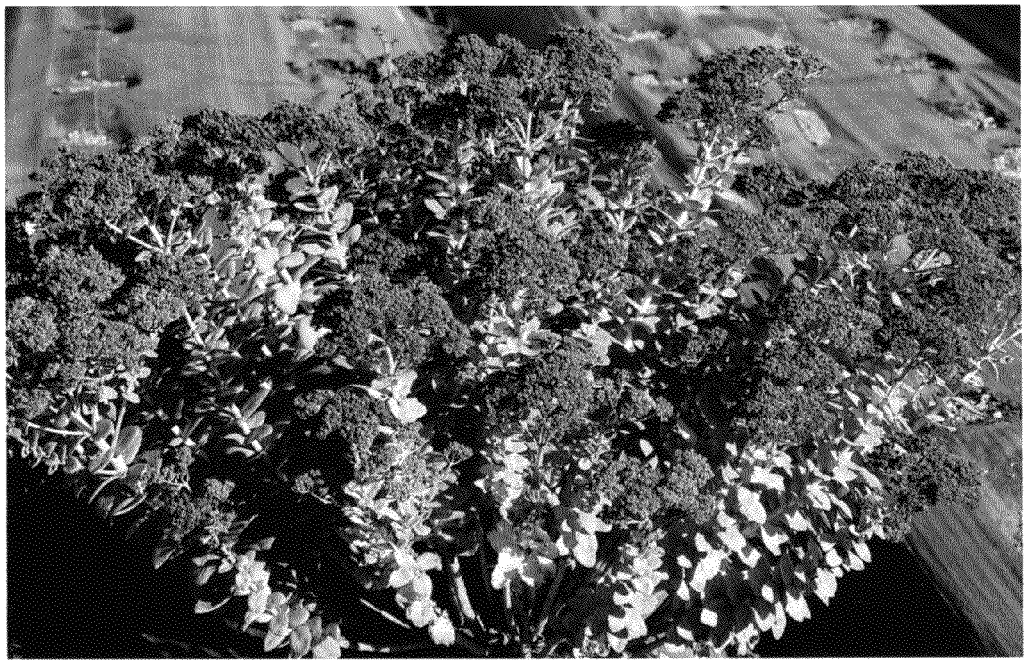

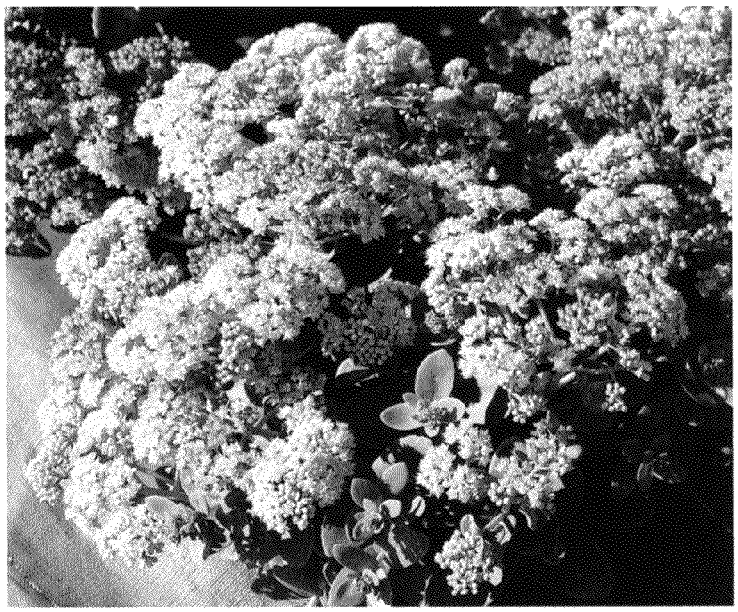
FIG. 3 above, FIG. 4 below